United States Patent

Shiraki et al.

[11] Patent Number: 5,824,831
[45] Date of Patent: Oct. 20, 1998

[54] CATALYST FOR DEHYDROGENATION OF ALKYL AROMATIC HYDROCARBON AND PROCESS FOR PRODUCTING VINYL AROMATIC HYDROCARBON USING THE SAME

[75] Inventors: Yasushi Shiraki, Tokuyama; Junshi Matsui, Ichihara, both of Japan

[73] Assignee: Idemitsu Petrochemical Co., Ltd., Tokyo, Japan

[21] Appl. No.: 676,451

[22] Filed: Jul. 8, 1996

[51] Int. Cl.[6] .............................. C07C 5/333; B01J 23/78
[52] U.S. Cl. .......................... 585/444; 585/440; 502/330
[58] Field of Search ............................. 502/330, 74, 298; 585/440, 444

[56] References Cited

U.S. PATENT DOCUMENTS

| | | | |
|---|---|---|---|
| 4,960,583 | 10/1990 | Rousset et al. | 423/633 |
| 4,963,343 | 10/1990 | Watson et al. | 423/594 |
| 4,975,407 | 12/1990 | Dejaifve et al. | 502/330 |
| 5,689,023 | 11/1997 | Hamilton, Jr. | 585/444 |

FOREIGN PATENT DOCUMENTS

| | | |
|---|---|---|
| 58-177148 | 10/1983 | Japan . |
| 59-120244 | 7/1984 | Japan . |
| 59-123537 | 7/1984 | Japan . |
| 59-216634 | 12/1984 | Japan . |
| 61-90741 | 5/1986 | Japan . |

*Primary Examiner*—Bekir L. Yildirim
*Attorney, Agent, or Firm*—Frishauf, Holtz, Goodman, Langer & Chick, P.C.

[57] ABSTRACT

An iron oxide catalyst for dehydrogenation of an alkyl aromatic hydrocarbon, wherein the catalyst is produced by adding potassium oxide to an iron oxide. The catalyst contains potassium ferrite. The catalyst has a ratio of a pore volume having a pore diameter of from 20 to 100 nm to a pore volume having a pore diameter of from 0 to 100 nm of between 0.7 and 9.0. The catalyst exhibits an excellent initial activity and has a substantially long catalyst life.

16 Claims, 1 Drawing Sheet

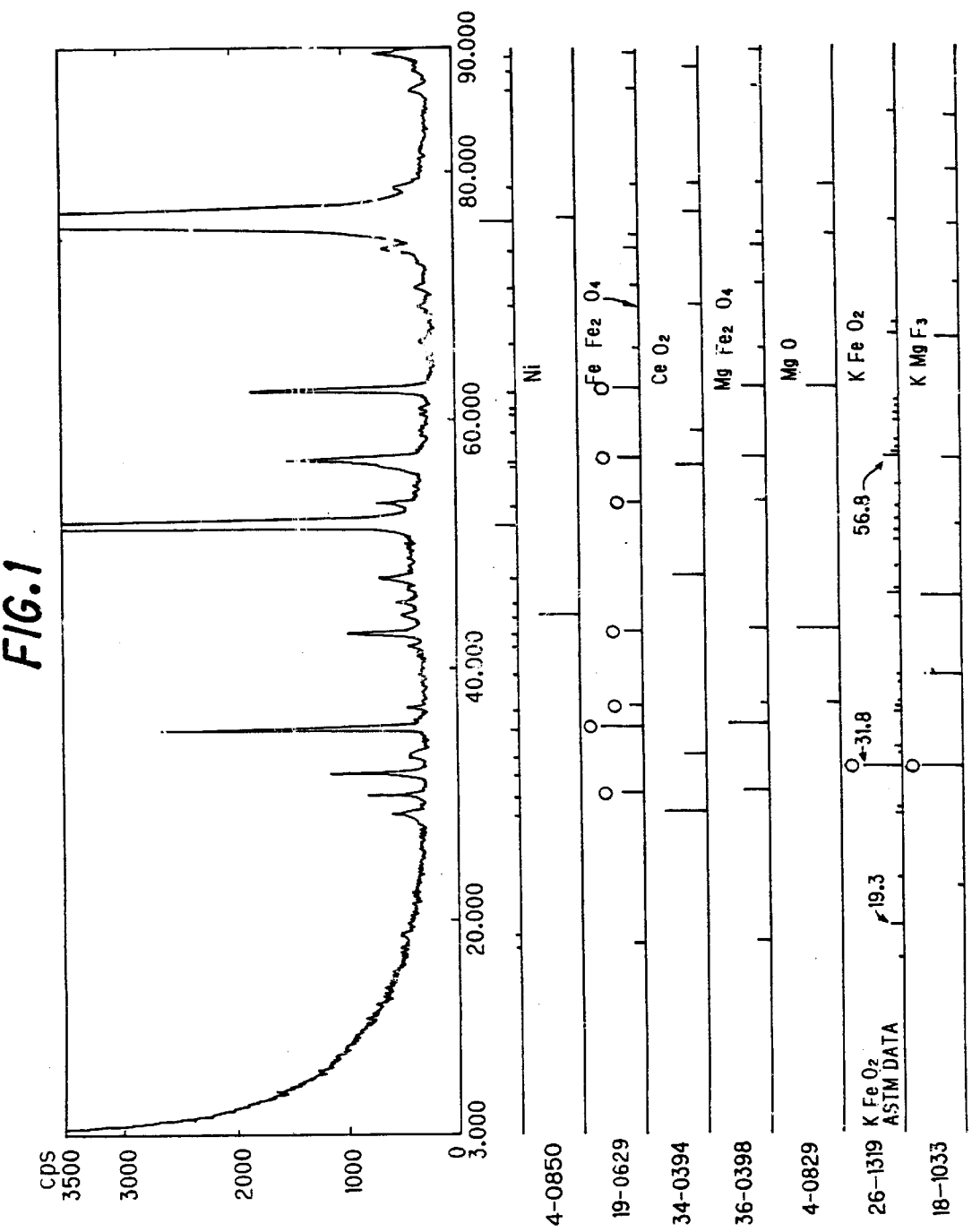

5,824,831

CATALYST FOR DEHYDROGENATION OF ALKYL AROMATIC HYDROCARBON AND PROCESS FOR PRODUCTING VINYL AROMATIC HYDROCARBON USING THE SAME

FIELD OF THE INVENTION

The present invention relates to a catalyst for dehydrogenation of an alkyl aromatic hydrocarbon, and to a process for producing a vinyl aromatic hydrocarbon using the same. More specifically, the present invention relates to a novel catalyst for dehydrogenation having a long catalyst life wherein the catalyst is an iron oxide catalyst and is produced by adding potassium oxide to iron oxide, characterized in that potassium ferrite is present, and a ratio of a pore volume having a pore diameter of from 20 to 100 nm is between 0.7 and 0.9 when a pore volume having a pore diameter of from 0 to 100 nm is defined as 1, and to a process which can produce a vinyl aromatic hydrocarbon from an alkyl aromatic hydrocarbon efficiently for a long period of time.

PRIOR ART

Vinyl aromatic hydrocarbons such as styrene and the like have been produced so far by dehydrogenating alkyl aromatic hydrocarbons in the presence of a catalyst. Heretofore, an iron oxide catalyst has been generally used as a catalyst for dehydrogenation.

With respect to the catalyst for dehydrogenation, improvements of catalytic activity such as an increase in the dehydrogenation activity, an extension of the catalyst life and the like have been conducted by the addition of various catalyst components. For example, a catalyst for dehydrogenation containing an alkali metal and an alkaline-earth metal [Japanese Laid-Open Patent Application (hereinafter referred to as "Japanese Kokai") No. 216,634/1984], a catalyst for dehydrogenation containing potassium oxide and magnesium oxide (Japanese Kokai No. 90,741/1986], a catalyst for dehydrogenation containing potassium oxide and cerium oxide (Japanese Kokai No. 177,148/1983), and a catalyst for dehydrogenation containing rare-earth metal compounds such as potassium oxide, chromium oxide and lanthanum oxide (Japanese Kokai Nos. 123,537/1984 and 120,244/1984) have been already known.

Further, a method is known in which a catalyst is preliminarily treated to improve catalytic activity. In general, the dehydrogenation of an alkyl aromatic hydrocarbon is started as follows. First of all, a catalyst for dehydrogenation is filled in a reactor, and the reactor is gradually heated approximately to a reaction temperature using a nitrogen gas. The nitrogen gas is then replaced with steam, and the temperature is elevated to the dehydrogenation temperature. Thereafter, an alkyl aromatic hydrocarbon such as ethylbenzene or the like is introduced into the reactor.

The activity of the catalyst for dehydrogenation which is used in the reaction gradually increased at the initial stage to obtain a desired activity. Then, the activity of the catalyst gradually decreased over the course of time. This behavior of a catalyst activity is the same with the above-mentioned catalysts.

It has been proposed that the catalyst for dehydrogenation be treated with hydrogen at 650° C. to increase the activity of the catalyst at the initial stage of the reaction.

This method is advantageous in that the activity of the catalyst can be improved through such a relatively simple procedure as the hydrogen treatment is conducted at the initial stage of the reaction without changing the composition of the catalyst for dehydrogenation.

The catalyst obtained by this method exhibits a high activity at the initial stage of the reaction compared to a catalyst which does not undergo the hydrogen treatment. However, after a couple of hours, the activity of the former catalyst becomes approximately the same as the activity of the latter catalyst.

SUMMARY OF THE INVENTION

The present inventors have assiduously conducted studies to solve the above-mentioned problems associated with the prior art. As a result, it has been surprisingly found that a catalyst which is obtained by reducing an iron oxide catalyst with hydrogen at a relatively low temperature exhibits an excellent activity as a catalyst for dehydrogenation and has an extremely long life. This finding has led to the completion of the present invention.

That is, the present invention provides a catalyst for dehydrogenation of an alkyl aromatic hydrocarbon wherein the catalyst is an iron oxide catalyst and is produced by adding potassium oxide to iron oxide, characterized in that potassium ferrite is present, and a ratio of a pore volume having a pore diameter of from 20 to 100 nm is between 0.7 and 0.9 when a pore volume having a pore diameter of from 0 to 100 nm is defined as 1.

The present invention provides a catalyst for dehydrogenation of an alkyl aromatic hydrocarbon wherein the catalyst is an iron oxide catalyst and is produced by adding potassium oxide to iron oxide, characterized in that potassium ferrite is present, a ratio of a pore volume having a pore diameter of from 20 to 100 nm is between 0.7 and 0.9 when a pore volume having a pore diameter of from 0 to 100 nm is defined as 1, and a specific surface area is between 1 and 2.5 $m^2/g$.

The present invention further provides a catalyst for dehydrogenation of an alkyl aromatic hydrocarbon in which the catalyst is obtained by reducing an iron oxide catalyst with hydrogen at a temperature of from 350° to 600° C.

The present invention is also directed to a catalyst for dehydrogenation of an alkyl aromatic hydrocarbon in which the catalyst is obtained by reducing an iron oxide catalyst with hydrogen at a temperature of from 350° to 600° C. and a gas hourly space velocity of 5 $hr^{-1}$ or more for 1 hour or more.

The present invention is further directed to a catalyst for dehydrogenation of an alkyl aromatic hydrocarbon in which the catalyst is obtained by reducing an iron oxide catalyst with hydrogen at a temperature of from 350° to 600° C. and a gas hourly space velocity of 5 $hr^{-1}$ or more for 5 to 30 hours.

The present invention also relates to a process for producing a vinyl aromatic hydrocarbon, which comprises dehydrogenating an alkyl aromatic hydrocarbon in the presence of a catalyst, characterized in that the first catalyst of the present invention is used.

Finally, the present invention further relates to a process for producing a vinyl aromatic hydrocarbon, which comprises dehydrogenating an alkyl aromatic hydrocarbon in the presence of a catalyst, characterized in that the third catalyst of the present invention is used.

BRIEF DESCRIPTION OF THE DRAWINGS

FIG. 1 is an X-ray diffraction pattern of a catalyst for dehydrogenation of an alkyl aromatic hydrocarbon in the present invention.

DESCRIPTION OF THE PREFERRED EMBODIMENTS

In the present invention, potassium ferrite refers to $K_2Fe_2O_4$ (also $KFeO_2$). The presence of potassium ferrite means that peaks are present at the following diffraction angles in the X-ray diffraction analysis (irradiation: Cu—Ka, wave length: 1.5418 Å).

2θ=19.3° (M=medium), 31.8° (VS=very strong), 56.8° (S=strong)

The first catalyst for dehydrogenation of an alkyl aromatic hydrocarbon in the present invention is an iron oxide catalyst and is produced by adding potassium oxide to iron oxide, characterized in that potassium ferrite is present, and a ratio of a pore volume having a pore diameter of from 20 to 100 nm is between 0.7 and 0.9 when a pore volume having a pore diameter of from 0 to 100 nm is defined as 1, namely, a ratio of a pore volume having a pore diameter of from 20 to 100 nm to a pore volume having a pore diameter of from 0 to 100 nm is between 0.7 and 0.9 (in other words, a percentage of a pore volume having a pore diameter of from 20 to 100 nm to a pore volume having a pore diameter of from 0 to 100 nm is between 70 and 90%).

The iron oxide catalyst here referred to is composed mainly of iron oxide ($Fe_2O_3$), and the iron oxide catalyst is produced by adding potassium oxide to iron oxide. Usually, the amount of iron oxide is between 40 and 80% by weight. Further, the catalyst contains a potassium component such as potassium oxide ($K_2O$) or the like preferably in an amount of from 5 to 30% by weight.

This iron oxide catalyst may contain small amounts of other catalyst components, for example, an alkaline-earth metal compound such as calcium oxide (usually less than 3% by weight) and chromium oxide (usually less than 4% by weight). Further, this catalyst may contain approximately 10% by weight or less of magnesium oxide, approximately 6% by weight or less of cerium oxide, and approximately 3% by weight or less of molybdenum oxide as required. Still further, this catalyst may contain a rare-earth metal compound such as lanthanum oxide or the like.

The catalyst can be used in various shapes. Usually, it takes the shape of a pellet having a diameter of from approximately 2 to 4 mm and a length of from approximately 3 to 10 mm.

The first catalyst for dehydrogenation of the alkyl aromatic hydrocarbon in the present invention is an iron oxide catalyst and is produced by adding potassium oxide to iron oxide, and potassium ferrite is present therein.

In this catalyst for dehydrogenation of an alkyl aromatic hydrocarbon, a ratio of a pore volume having a pore diameter of from 20 to 100 nm has to be between 0.7 and 0.9 when a pore volume having a pore diameter of from 0 to 100 nm is defined as 1.

The first catalyst for dehydrogenation in the present invention is obtained by reducing the iron oxide catalyst with hydrogen under specific conditions as will be later described in the third catalyst. The presence of potassium ferrite and the pore volume described herein were determined by studying a relation with optimum conditions for reduction with hydrogen.

That is, it has been found that in the catalyst obtained by reducing the iron oxide catalyst with hydrogen under specific conditions, potassium ferrite is present and the ratio of the pore volume having the pore diameter of from 20 to 100 nm is between 0.7 and 0.9 when a pore volume having a pore diameter of from 0 to 100 nm is defined as 1, and that this catalyst can have an extended catalyst life while maintaining the initial activity of the catalyst as compared to a catalyst which does not undergo the reduction with hydrogen.

Further, in the second catalyst of the present invention, the specific surface area is between 1 and 2.5 $m^2/g$, preferably between 1.5 and 2.0 $m^2/g$.

The amount of the active site was measured through an XRD spectrum.

This measurement was conducted using an X-ray diffraction apparatus comprising an X-ray diffraction device (RINT 1500, manufactured by Rigaku K.K.) and a monochromator fitted therewith. A sample was filled in this apparatus in a nitrogen atmosphere, and the apparatus was sealed with an Ni foil. The measurement conditions are as follows.

[Measurement conditions]

Tube ball: Cu
Voltage: 60 kV
Standard $Fe_3O_4$
Current: 300 mA
Slit type: DS-1°, RS-0.15 mm, SS-1°
Scanning speed: 2.0°/min
Sampling interval: 0.01°

With respect to the catalyst obtained through the reduction pretreatment with hydrogen in the present invention (first catalyst of the present invention), a catalyst that does not undergo the pretreatment, and a catalyst obtained by an ordinary start-up method at a high ratio of high steam to oil (hereinafter referred to as "high S/O") [a reaction is conducted at high S/O (S/O=3.0 (weight ratio)) for 6 days and then at usual S/O=1.5 (weight ratio)], the reaction was conducted for approximately 1 day, and the amount of each active site was measured. As a result, $K_2Fe_2O_4$ (potassium ferrite) was found in the catalyst obtained through the reduction pretreatment with hydrogen of the present invention (refer to FIG. 1.).

Further, according to the studies of the present inventors, it was found that the reduction with hydrogen is preferably conducted at 500° C. for 24 hours, as will be later described in Example 6. Therefore, the reduction conditions and the reduction time with hydrogen were examined.

First, the reduction conditions with hydrogen of the catalyst and the properties of the catalyst (specific surface area and pore distribution) were examined with respect to Example 6.

The specific surface area and the pore volume were measured by a fixed amount gas adsorption method using a Belsorp 36 (manufactured by Nippon Bell K.K.) as a measurement device.

It was found that when the reduction time with hydrogen is longer, the specific surface area first becomes larger, and then becomes smaller, and that when a hydrogen flow rate is as high as 100 ml/min, the specific surface area tends to decrease.

Considering the reduction conditions with hydrogen at 500° C. and for 24 hours and the range of up to approximately 20 hours, it was found that the specific surface area is preferably between 1 and 2.5 $m^2/g$.

It was further found that when the reduction time with hydrogen is rendered longer at a reduction temperature with hydrogen of 500° C., micropores are gradually ruptured into mesopores which are then shifted into macropores.

Accordingly, it was found that in the pore distribution, it is preferable to rupture micropores and increase macropores as much as possible, and that a ratio of a pore volume having a pore diameter of from 20 to 100 nm is preferably between 0.7 and 0.9 when a pore volume having a pore diameter of from 0 to 100 nm is defined as 1.

Meanwhile, when the hydrogenation reduction time is longer in the hydrogen reduction at 400° C., micropores are gradually ruptured and shifted into mesopores.

However, when the hydrogen flow rate is increased (doubled), it is possible that even in the reduction with hydrogen at 400° C., micropores and mesopores are eliminated and only macropores are formed.

The reduction with hydrogen at 400° C. for 24 hours with a doubled hydrogen flow rate (Example 3) gives an excellent catalytic activity and an excellent catalyst life compared to the reduction with hydrogen at 500° C. for 24 hours (Example 1). Thus, the reduction with hydrogen conducted at 500° C. for 24 hours appears to be excessive.

Consequently, the specific surface area and the catalytic activity do not correlate in the untreated catalyst (NEW, spent). However, when the catalyst is reduced with hydrogen, the degree of the reduction with hydrogen can be known from the properties of the catalyst (specific surface area and pore diameter), and the catalytic activity and the catalyst life can be determined to some extent.

As mentioned above, the specific surface area of the catalyst is between 1 and 2.5 $m^2/g$, and it is preferable to rupture micropores and increase macropores as much as possible in the pore distribution.

The present invention provides a catalyst for dehydrogenation of an alkyl aromatic hydrocarbon in which the catalyst is obtained by reducing an iron oxide catalyst with hydrogen at a temperature of from 350° to 600° C. The thus-obtained catalyst is the first and second catalysts for dehydrogenation of the alkyl aromatic hydrocarbon in the present invention. That is, the first and second catalysts for dehydrogenation of the alkyl aromatic hydrocarbon can be produced by, for example, the method which is thirdly described in the present invention.

The third catalyst for dehydrogenation of the alkyl aromatic hydrocarbon in the present invention is obtained by reducing the iron oxide catalyst with hydrogen at a temperature of from 350° to 600° C.

The iron oxide catalyst here referred to is, as mentioned above, a catalyst which is composed mainly of iron oxide ($Fe_2O_3$), and the iron oxide catalyst is produced by adding potassium oxide to iron oxide. The content of iron oxide is usually between 40 and 80% by weight, and this catalyst contains a potassium compound such as potassium oxide ($K_2O$) or the like preferably in an amount of from 5 to 30% by weight. This iron oxide catalyst may further contain small amounts of other catalyst components, for example, an alkaline-earth metal compound such as calcium oxide (usually less than 3% by weight) and chromium oxide (usually less than 4% by weight). Still further, it may contain approximately 10% by weight or less of magnesium oxide, approximately 6% by weight or less of cerium oxide and approximately 3% by weight or less of molybdenum oxide as required. Furthermore, it may contain a rare-earth metal compound such as lanthanum oxide.

The catalyst can take various shapes. Usually it takes a shape of a pellet having a diameter of from 2 to 4 mm and a length of from 3 to 10 mm.

The third catalyst for dehydrogenation of the alkyl aromatic hydrocarbon in the present invention is thus obtained by reducing such an iron oxide catalyst with hydrogen.

The reduction temperature with hydrogen is between 350° and 600° C., preferably between 400° and 500° C. When the reduction temperature with hydrogen is lower than 350° C., the reduction rate with hydrogen is notably decreased. As a result, a desired degree of reduction is not obtained, and a catalyst decline rate is increased, making it impossible to obtain a catalyst having a long life. Meanwhile, when the reduction temperature with hydrogen exceeds 600° C., the activity of the catalyst is decreased. The reduction time with hydrogen depends on the reduction temperature with hydrogen. It is usually 1 hour or more, preferably between 5 and 30 hours. When the reduction temperature with hydrogen is low, it is advisable to increase the flow rate with hydrogen or to make the reduction time with hydrogen longer.

Hydrogen which is used in the reduction may contain a gas which is inert to the dehydrogenation, such as nitrogen, methane or the like. Further, a reduction gas may contain steam in addition to hydrogen. In this case, a molar ratio of hydrogen to water ($H_2/H_2O$) is preferably 0.05 or more, more preferably 0.5 or more.

With respect to the flow rate of hydrogen, a gas hourly space velocity (GHSV) of pure hydrogen is preferably 5 $hr^{-1}$ or more, more preferably between 20 and 300 $hr^{-1}$. The pressure is not particularly limited. The reduction can be conducted either under increased pressure or under reduced pressure.

In the present invention, the vinyl aromatic hydrocarbon is produced by dehydrogenating the alkyl aromatic hydrocarbon in the presence of the above-mentioned first catalyst for dehydrogenation of the present invention.

As the alkyl aromatic hydrocarbon, an aromatic hydrocarbon having 1 or more alkyl groups that form a vinyl group through the dehydrogenation is used. Specific examples thereof include ethylbenzene and diethylbenzene. The benzene nucleus may have a substituent which does not participate in the dehydrogenation, for example, an alkyl group such as an methyl group or the like, or a halogen atom such as chlorine or the like.

In this dehydrogenation, the temperature is usually between 600° and 660° C., preferably between 610° and 640° C. The pressure is usually between 200 and 600 torrs, preferably between 300 and 500 torrs. A weight ratio of steam to alkyl aromatic hydrocarbon (steam/alkyl aromatic hydrocarbon) is usually between 1.0/1 and 3.0/1, preferably between 1.5/1 and 2.0/1. The liquid hourly space velocity (LHSV) of the alkyl aromatic hydrocarbon is usually between 0.2 and 20 $hr^{-1}$, preferably between 0.5 and 1.0 $hr^{-1}$.

In the present invention, the alkyl aromatic hydrocarbon is dehydrogenated in the presence of the above-mentioned third catalyst of the present invention to produce the vinyl aromatic hydrocarbon. The alkyl aromatic hydrocarbon and the conditions for the dehydrogenation are the same as those described sixthly in the present invention.

In the above-mentioned manner, the vinyl aromatic hydrocarbon is produced from the alkyl aromatic hydrocarbon; for example, styrene is produced from ethylbenzene.

EXAMPLES

The present invention is illustrated more specifically by referring to the following Examples and Comparative Examples.

The following catalyst and reaction tube were used in the following Examples and Comparative Examples.

A commercially available catalyst for dehydrogenation of ethylbenzene (G-84C, made by Nissan Girdler K.K.;

composition=77 wt. % $Fe_2O_3$, 10 wt. % $K_2O$, 5.0 wt. %. $Ce_2O_3$, 2.5 wt %. $MoO_3$, 2.2 wt. % CaO, 2.2 wt. % MgO, and less than 0.1 wt. % of $Cr_2O_3$; shape=pellet 3.2 mm in diameter) was used.

A reaction tube having a diameter of 1 inch (inner diameter=21.4 mm) and a length of 60 cm was used, and 100 cc (132 g) of the above-mentioned catalyst was filled therein. Alumina balls having a diameter of ⅛ inch were filled in an upper layer of a catalyst bed in the reaction tube, and the lower portion of the catalyst bed was fixed by means of a grating. The inner temperature of the reaction tube was controlled using an electric furnace which was divided into three parts and which was mounted on the outer surface of the reaction tube. A thermowell having an outer diameter of 6 mm was inserted into the reaction tube to determine the temperatures of the upper, middle and lower portions of the catalyst bed and to control the temperatures of each portions of the catalyst bed to the reaction temperature (620° C. in Example 1) using this divided electric furnace. The reaction was conducted through the downward flow.

Example 1

(1) Production of a catalyst obtained through hydrogen reduction

The above-mentioned reaction tube was filled with 100 cc (132 g) of the catalyst as mentioned above. The inside of the system was evacuated (460 torrs), and a nitrogen gas was caused to flow at a rate of 3 liters/hr. When the catalyst bed was heated to 500° C. at a rate of temperature rise of 100° C./hr, the nitrogen gas was replaced with a hydrogen gas, and the reduction of the catalyst with hydrogen was conducted at 500° C. for 24 hours at a flow rate of 3 liters/hr (GHSV=30 $hr^{-1}$).

In this manner, a catalyst was produced in which potassium ferrite was present and a ratio of a pore volume having a pore diameter of from 20 to 100 nm was 0.86 when a pore volume having a pore diameter of from 0 to 100 nm was defined as 1 (in other words, a percentage of a pore volume having a pore diameter of from 20 to 100 nm to a pore volume having a pore diameter of from 0 to 100 nm was 86%). The X-ray diffraction pattern of the resulting catalyst is shown in FIG. 1.

(2) Production of a vinyl aromatic hydrocarbon

After the catalyst was reduced with hydrogen, the flow of the hydrogen gas stopped. Then, a steam was caused to flow at a rate of 150 g/hr. When the temperature was elevated to 550° C. at a rate of temperature rise of 100° C./hr, ethylbenzene was caused to flow at a flow rate of 100 g/hr. A weight ratio of steam to ethylbenzene was 1.5, and the liquid hourly space velocity (LHSV) of ethylbenzene was 1.0 $hr^{-1}$.

Thereafter, the temperature was elevated to 620° C. at a rate of temperature rise of 100° C./hr, and the dehydrogenation of ethylbenzene was continued at 620° C. for 3 months. The initial activity of the catalyst and the catalyst decline rate were then evaluated. The activity of the catalyst was evaluated in terms of the concentration (% by weight) of styrene (SM) in the resulting solution. The catalyst decline rate was evaluated in terms of an amount (ΔSM) of styrene decreased in the resulting solution per day (% by weight/day). The results are shown in Table 1.

Example 2

(1) Production of a catalyst obtained through reduction with hydrogen

A catalyst was reduced with hydrogen in an atmosphere of a nitrogen gas in the same manner as in (1) of Example 1 except that the temperature was elevated to 600° C. in an atmosphere of a nitrogen gas, the nitrogen gas was then replaced with a hydrogen gas at 600° C., and the reduction of the catalyst with hydrogen was conducted at 600° C. for 2 hours at a hydrogen gas flow rate of 3 liters/hr.

In this manner, a catalyst was produced in which potassium ferrite was present and a ratio of a pore volume having a pore diameter of from 20 to 100 nm was 0.87 when a pore volume having a pore diameter of from 0 to 100 nm was defined as 1 (in other words, a percentage of a pore volume having a pore diameter of from 20 to 100 nm to a pore volume having a pore diameter of from 0 to 100 nm was 87%).

(2) Production of a vinyl aromatic hydrocarbon

After the catalyst was reduced with hydrogen, the hydrogen gas was replaced with a nitrogen gas, and the nitrogen gas was caused to flow at a flow rate of 3 liters/hr. The temperature was reduced to 500° C. at a rate of temperature fall of 100° C./hr. When the temperature reached 500° C., the flow of the nitrogen gas stopped, steam was then caused to flow at a rate of 150 g/hr, and ethylbenzene was caused to flow at a flow rate of 100 g/hr.

Subsequently, the dehydrogenation was continued, and the initial activity of the catalyst and the catalyst decline rate were evaluated in the same manner as in Example 1. The results are shown in Table 1.

Example 3

(1) Production of a catalyst obtained through reduction with hydrogen

A catalyst was reduced with hydrogen in an atmosphere of a nitrogen gas in the same manner as in (1) of Example 1 except that the temperature was elevated to 400° C. in an atmosphere of a nitrogen gas, the nitrogen gas was then replaced with a hydrogen gas at 400° C., and the reduction with hydrogen of the catalyst was conducted at 400° C. for 24 hours at a hydrogen gas flow rate of 6 liters/hr (GHSV= 60 $hr^{-1}$).

In this manner, a catalyst was produced in which potassium ferrite was present and a ratio of a pore volume having a pore diameter of from 20 to 100 nm was 0.82 when a pore volume having a pore diameter of from 0 to 100 nm was defined as 1 (in other words, a percentage of a pore volume having a pore diameter of from 20 to 100 nm to a pore volume having a pore diameter of from 0 to 100 nm was 82%).

(2) Production of a vinyl aromatic hydrocarbon

After the catalyst was reduced with hydrogen, the hydrogen gas was replaced with a nitrogen gas, and the nitrogen gas was caused to flow at a flow rate of 6 liters/hr. The temperature was elevated to 500° C. at a rate of temperature rise of 100° C./hr. When the temperature reached 500° C., the flow of the nitrogen gas stopped, steam was then caused to flow at a rate of 150 g/hr, and ethylbenzene was caused to flow at a flow rate of 100 g/hr.

Subsequently, the dehydrogenation was continued, and the initial activity of the catalyst and the catalyst decline rate were evaluated in the same manner as in Example 1. The results are shown in Table 1.

Example 4

(1) Production of a catalyst obtained through reduction with hydrogen

A catalyst was reduced with hydrogen in the same manner as in (1) of Example 1 except that the reduction temperature was 350° C., the reduction time was 36 hours and the hydrogen gas flow rate was 20 liters/hr (GHSV=200 hr$^{-1}$).

In this manner, a catalyst was produced in which potassium ferrite was present and a ratio of a pore volume having a pore diameter of from 20 to 100 nm was 0.83 when a pore volume having a pore diameter of from 0 to 100 nm was defined as 1 (in other words, a percentage of a pore volume having a pore diameter of from 20 to 100 nm to a pore volume having a pore diameter of from 0 to 100 nm was 83%).

(2) Production of a vinyl aromatic hydrocarbon

The dehydrogenation was continued in the same manner as in (2) of Example 1 except that the catalyst obtained through the reduction with hydrogen in the above-mentioned (1) was used. The initial activity of the catalyst and the catalyst decline rate were evaluated as in Example 1. The results are shown in Table 1.

Comparative Example 1

Example 1 was repeated except that the reduction of the catalyst with hydrogen was not conducted. The initial activity of the catalyst and the catalyst decline rate were evaluated as in Example 1. The results are shown in Table 1.

In this manner, a catalyst was produced in which potassium ferrite was present and a ratio of a pore volume having a pore diameter of from 20 to 100 nm was 0.65 when a volume of a pore having a pore diameter of from 0 to 100 nm was defined as 1 (in other words, a percentage of a pore volume having a pore diameter of from 20 to 100 nm to a pore volume having a pore diameter of from 0 to 100 nm was 65%).

Comparative Example 2

(1) Production of a catalyst obtained through reduction with hydrogen

The reduction with hydrogen of a catalyst was conducted in the same manner as in (1) of Example 1 except that the reduction temperature was 650° C. and the reduction time was 2 hours.

In this manner, a catalyst was produced in which potassium ferrite was present and a ratio of a pore volume having a pore diameter of from 20 to 100 nm was 0.92 when a pore volume having a pore diameter of from 0 to 100 nm was defined as 1 (in other words, a percentage of a pore volume having a pore diameter of from 20 to 100 nm to a pore volume having a pore diameter of from 0 to 100 nm was 92%).

(2) Production of a vinyl aromatic hydrocarbon

The dehydrogenation was continued in the same manner as in (2) of Example 1 except that the catalyst obtained through the reduction with hydrogen in the above-mentioned (1) was used. The initial activity of the catalyst and the catalyst decline rate were evaluated as in (2) of Example 1. The results are shown in Table 1.

Comparative Example 3

(1) Production of a catalyst obtained through reduction with hydrogen

The reduction with hydrogen of a catalyst was conducted in the same manner as in (1) of Example 1 except that the reduction temperature was 300° C., the reduction time was 36 hours, and the hydrogen gas flow rate was 20 liters/hr (GHSV=200 hr$^{-1}$).

(2) Production of a vinyl aromatic hydrocarbon

The dehydrogenation was continued in the same manner as in (2) of Example 1 except that the catalyst obtained through the reduction with hydrogen in the above-mentioned (1) was used. The initial activity of the catalyst and the catalyst decline rate were evaluated as in (2) of Example 1. The results are shown in Table 1.

Example 5

(1) Production of a catalyst obtained through reduction with hydrogen

A catalyst was reduced with hydrogen in the same manner as in (1) of Example 1 except that water (steam) was present at a molar ratio of hydrogen gas to water (steam) of 1.5.

In this manner, a catalyst was produced in which potassium ferrite was present and a ratio of a pore volume having a pore diameter of from 20 to 100 nm was 0.84 when a pore volume having a pore diameter of from 0 to 100 nm was defined as 1 (in other words, a percentage of a pore volume having a pore diameter of from 20 to 100 nm to a pore volume having a pore diameter of from 0 to 100 nm was 84%).

(2) Production of a vinyl aromatic hydrocarbon

The dehydrogenation was continued in the same manner as in (2) of Example 1 except that the catalyst obtained through the reduction with hydrogen in the above-mentioned (1) was used. The initial activity of the catalyst and the catalyst decline rate were evaluated as in (2) of Example 1. The results are shown in Table 1.

When using the catalyst obtained through the reduction with hydrogen in the presence of water (steam) at a molar ratio of hydrogen gas to water (steam) of 0.02, the initial activity of the catalyst was 68.9% by weight, and it was equal to that of the catalyst in Example 5, but the catalyst decline rate was as high as −0.083 (% by weight/day).

Example 6

(1) Production of a catalyst obtained through reduction with hydrogen $Fe_2O_3$ and $K_2CO_3$ were weighed at a desired weight ratio ($Fe_2O/K_2CO_3$=8), and were mixed well. The mixture was molded and classified (from 20 to 60 mesh). The resulting product was burned at 500° C. for 24 hours to form a catalyst.

The reaction tube was filled with 100 cc (132 g) of this catalyst, the inside of the system was evacuated (460 torrs), and a nitrogen gas was caused to flow at a rate of 3 liters/hr as in Example 1. When the catalyst bed was heated to 500° C. at a rate of temperature rise of 100° C./hr, the nitrogen gas was replaced with a hydrogen gas, and the reduction with hydrogen of the catalyst was conducted at 500° C. for 24 hours at a flow rate of 3 liters/hr (GHSV=30 hr$^{-1}$).

In this manner, a catalyst was produced in which potassium ferrite was present and a ratio of a pore volume having a pore diameter of from 20 to 100 nm was 0.84 when a pore volume having a pore diameter of from 0 to 100 nm was defined as 1 (in other words, a percentage of a pore volume having a pore diameter of from 20 to 100 nm to a pore volume having a pore diameter of from 0 to 100 nm was 84%).

(2) Production of a vinyl aromatic hydrocarbon

The dehydrogenation was continued in the same manner as in (2) of Example 1 except that the catalyst obtained through the reduction with hydrogen in the above-mentioned (1) was used. The initial activity of the catalyst and the catalyst decline rate were evaluated as in Example 1. The results are shown in Table 1.

TABLE 1

|  | Conditions for reduction with hydrogen | | | Concentration of styrene formed (% by weight) | Catalyst decline rate [Δ SM] (% by weight/day) |
| --- | --- | --- | --- | --- | --- |
|  | Temperature (% °C.) | Time (hr) | Hydrogen flow rate (liter/hr) | | |
| Ex. 1 | 500 | 24 | 3 | 69.7 | −0.033 |
| Ex. 2 | 600 | 2 | 3 | 69.6 | −0.044 |
| Ex. 3 | 400 | 24 | 6 | 72.3 | −0.021 |
| Ex. 4 | 350 | 36 | 20 | 71.6 | −0.026 |
| CEx. 1 | no reduction with hydrogen | | | 69.5 | −0.085 |
| CEx. 2 | 650 | 2 | 3 | 64.3 | −0.050 |
| CEx. 3 | 300 | 36 | 20 | 68.7 | −0.084 |
| Ex. 5 | 500 | 24 | 6* | 70.3 | −0.038 |
| Ex. 6 | 500 | 24 | 3 | 70.0 | −0.035 |

Ex. - Example, CEx. - Comparative Example
*Water (steam) was added at a molar ratio of hydrogen gas to water (steam) of 1.5.

The results of Table 1 reveal the following.

(1) When the catalyst is reduced with hydrogen at 500° C. (Example 1) and 600° C. (Example 2), the initial activity of the catalyst is equal to that of the catalyst that does not undergo the hydrogen reduction (Comparative Example 1). However, the catalyst decline rate of the former catalyst is markedly reduced to from 1/3 to 1/2 that of the latter catalyst.

(2) When the reduction with hydrogen is conducted for a long period of time using a large amount of a hydrogen gas (in Example 3, the hydrogen flow rate is 6 liters/hr, GHSV is 60 hr$^{-1}$, and the reduction time is 24 hours; in Example 4, the hydrogen flow rate is 20 liters/hr, GHSV is 200 hr$^{-1}$, and the reduction time is 36 hours), the yield of styrene is increased even at the low temperature (400° C. in Example 3 and 350° C. in Example 4), and the catalyst decline rate is markedly reduced to less than 1/3 that of the catalyst that does not undergo the reduction with hydrogen (Comparative Example 1).

(3) When the reduction of the catalyst with hydrogen is conducted at the high temperature (650 ° C.) as in Comparative Example 2, the catalyst decline rate is reduced, but the initial activity of the catalyst is decreased.

(4) When the reduction of the catalyst with hydrogen is conducted at the low temperature (300° C.) as in Comparative Example 3, the initial activity of the catalyst is low and the catalyst decline rate is high even if the hydrogen gas flow rate is as high as 20 liters/hr and the reduction time is 36 hours.

(5) Even when water (steam) is present not in the dehydrogenation but in the reduction of the catalyst with hydrogen, the catalyst can exhibit the excellent initial activity and reduce the catalyst decline rate (Example 5). However, when the molar ratio of hydrogen gas to water (steam) is less than 0.5, the catalyst decline rate is increased, and no effect of the reduction with hydrogen is observed.

EFFECTS OF THE INVENTION

The catalyst for dehydrogenation of the alkyl aromatic hydrocarbon in the present invention is an iron oxide catalyst and is produced by adding potassium oxide to an iron oxide wherein potassium ferrite is present, and a ratio of a pore volume having a pore diameter of from 20 to 100 nm is between 0.7 and 0.9 when a pore volume having a pore diameter of from 0 to 100 nm is defined as 1. It is a novel catalyst which has not been found so far.

Such a catalyst of the present invention is obtained by reducing the iron oxide catalyst with hydrogen at a temperature of from 350° to 600° C. The catalyst life can be extended, by conducting the reduction of the catalyst with hydrogen before the dehydrogenation reaction, while making the initial activity of the catalyst equal to that of the catalyst obtained without conducting the reduction with hydrogen.

Thus, the catalyst of the present invention exhibits an excellent initial activity and has quite a long catalyst life.

Consequently, the catalyst of the present invention is especially preferable as a catalyst for dehydrogenation of an alkyl aromatic hydrocarbon.

Further, in accordance with the present invention, since the alkyl aromatic hydrocarbon is dehydrogenated in the presence of such a catalyst, the vinyl aromatic hydrocarbon can be produced for a long period of time at good efficiency.

What is claimed is:

1. A catalyst for dehydrogenation of an alkyl aromatic hydrocarbon, the catalyst being produced by adding potassium oxide to iron oxide and reducing the resultant product with hydrogen, the catalyst comprising potassium ferrite of the formula $K_2Fe_2O_4$ or $KFeO_2$, and the catalyst having a ratio of a pore volume having a pore diameter of 20 to 100 nm to a pore volume having a pore diameter of 0 to 100 nm of between 0.7 and 0.9.

2. A catalyst for dehydrogenation of an alkyl aromatic hydrocarbon, the catalyst being produced by adding potassium oxide to iron oxide and reducing the resultant product with hydrogen, the catalyst comprising potassium ferrite of the formula $K_2Fe_2O_4$ or $KFeO_2$, a ratio of a pore volume having a pore diameter of from 20 to 100 nm to a pore volume having a pore diameter of from 0 to 100 nm of between 0.7 and 0.9, and having a specific surface area between 1 and 2.0 $m^2/g$.

3. The catalyst of claim 1, wherein the reduction with hydrogen is carried out at a temperature of form 350° to 600° C.

4. The catalyst of claim 3, wherein the reducing with hydrogen is carried out at a gas hourly space velocity of 5 $hr^{-1}$ or more for 1 hour or more.

5. The catalyst of claim 3, wherein the reducing with hydrogen is carried out at a gas hourly space velocity of 5 $hr^{-1}$ or more for from 5 to 30 hours.

6. A process for producing a vinyl aromatic hydrocarbon, which comprises dehydrogenating an alkyl aromatic hydrocarbon in the presence of a catalyst, wherein the catalyst is the catalyst of claim 1.

7. A process for producing a vinyl aromatic hydrocarbon, which comprises dehydrogenating an alkyl aromatic hydrocarbon in the presence of a catalyst, wherein the catalyst is the catalyst of claim 3.

8. The catalyst of claim 1, wherein the catalyst contains 40 to 80 weight % of iron oxide.

9. The catalyst of claim 8, wherein the catalyst contains 5 to 30 weight % of the potassium oxide.

10. The catalyst of claim 9, wherein the catalyst further comprises at least one additional component selected from the group consisting of an alkaline-earth metal compound, chromium oxide, magnesium oxide, cerium oxide, molybdenum oxide and a rare-earth metal compound.

11. The catalyst of claim 9, wherein the catalyst further comprises at least one additional component selected from the group consisting of less than 3 weight % of calcium oxide, less than 4 weight % of magnesium oxide, 6 weight % or less of cerium oxide, and 3 weight % or less of molybdenum oxide, and lanthanum oxide.

12. The catalyst of claim 2, wherein the specific surface area is 1.5 to 2.0 $m^2/g$.

13. The catalyst of claim 5, wherein the reducing with hydrogen is carried out at a temperature of 400° to 500° C. with a gas velocity of 20 to 300 $hr^{-1}$.

14. The process of claim 6, wherein the alkyl aromatic hydrocarbon is selected from the group consisting of ethylbenzene and diethylbenzene.

15. The process of claim 14, wherein the dehydrogenating is carried out at a temperature of 600° to 660° C., a pressure of 200 to 600 torrs, a weight ratio of steam to the alkyl aromatic hydrocarbon of between 1.0/1 to 3.0/1 and a liquid hourly space velocity of the alkyl aromatic compound of 0.2 to 20 $hr^{-1}$.

16. The process of claim 14, wherein the dehydrogenating is carried out at a temperature of 610° to 640° C., a pressure of 300 to 500 torrs, a weight ratio of steam to the alkyl aromatic hydrocarbon of between 1.5/1 to 2.0/1 and a liquid hourly space velocity of the alkyl aromatic compound of 0.5 to 1.0 $hr^{-1}$.

* * * * *

UNITED STATES PATENT AND TRADEMARK OFFICE
CERTIFICATE OF CORRECTION

PATENT NO.   : 5,824,831                                       Page 1 of 1
DATED        : October 20, 1998
INVENTOR(S)  : Yasushi Shiraki et al.

It is certified that error appears in the above-identified patent and that said Letters Patent is hereby corrected as shown below:

Title page,
Item [54], replace "PRODUCTING" with -- PRODUCING --.

Column 12, claim 3,
Line 43, replace "form" with -- from --.

Signed and Sealed this

Twenty-sixth Day of February, 2002

Attest:

JAMES E. ROGAN
*Attesting Officer*   *Director of the United States Patent and Trademark Office*